(12) United States Patent
Bynam et al.

(10) Patent No.: US 10,980,484 B2
(45) Date of Patent: Apr. 20, 2021

(54) METHOD OF ENABLING FEATURE EXTRACTION FOR GLUCOSE MONITORING USING NEAR-INFRARED (NIR) SPECTROSCOPY

(71) Applicant: SAMSUNG ELECTRONICS CO., LTD., Suwon-si (KR)

(72) Inventors: Kiran Bynam, Karnataka (IN); So Young Lee, Daejeon (KR); Sujit Jos, Karnataka (IN); Gorish Aggarwal, Karnataka (IN); Srikanth Mallavarapu Rama, Karnataka (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 161 days.

(21) Appl. No.: 15/937,295

(22) Filed: Mar. 27, 2018

(65) Prior Publication Data

US 2018/0271448 A1  Sep. 27, 2018

(30) Foreign Application Priority Data

Mar. 27, 2017 (IN) .............................. 201741010850
Mar. 6, 2018 (KR) ........................ 10-2018-0026210

(51) Int. Cl.
*A61B 5/1455* (2006.01)
*A61B 5/00* (2006.01)
*G16H 40/63* (2018.01)
*A61B 5/145* (2006.01)

(52) U.S. Cl.
CPC .......... *A61B 5/7203* (2013.01); *A61B 5/1455* (2013.01); *A61B 5/14532* (2013.01); *A61B 5/725* (2013.01); *G16H 40/63* (2018.01); *A61B 5/0075* (2013.01)

(58) Field of Classification Search
None
See application file for complete search history.

(56) References Cited

U.S. PATENT DOCUMENTS

| 6,990,364 B2 | 1/2006 | Ruchti et al. |
| 8,274,050 B2 | 9/2012 | Grimberg |
| 8,359,164 B2 | 1/2013 | Li |
| 9,316,628 B2 | 4/2016 | O'Brien et al. |

(Continued)

FOREIGN PATENT DOCUMENTS

| KR | 10-2011-0028559 A | 3/2011 |
| KR | 10-2015-0112902 A | 10/2015 |

(Continued)

OTHER PUBLICATIONS

Communication dated Aug. 21, 2018, issued by the European Patent Office in counterpart European Patent Application No. 18164204.2.

(Continued)

*Primary Examiner* — Marjan Fardanesh
(74) *Attorney, Agent, or Firm* — Sughrue Mion, PLLC

(57) ABSTRACT

A method of extracting glucose feature, a method for monitoring glucose using near-infrared (NIR) spectroscopy and a glucose monitoring device are provided. The method comprising: removing noise from a near-infrared (NIR) data; extracting a glucose signal from the NIR data; and removing temporal drift components from the extracted glucose signal.

14 Claims, 13 Drawing Sheets

(56) References Cited

U.S. PATENT DOCUMENTS

| | | | |
|---|---|---|---|
| 9,320,471 | B2 | 4/2016 | Hayes et al. |
| 2002/0123677 | A1 | 9/2002 | Miki et al. |
| 2004/0092804 | A1* | 5/2004 | Rebec .................. A61B 5/1495 600/310 |
| 2005/0107676 | A1 | 5/2005 | Acosta et al. |
| 2008/0210872 | A1 | 9/2008 | Grimberg |
| 2010/0324398 | A1 | 12/2010 | Tzyy-Ping |
| 2015/0305658 | A1 | 10/2015 | Islam |
| 2016/0091496 | A1* | 3/2016 | Xu ....................... A61B 5/1455 356/436 |

FOREIGN PATENT DOCUMENTS

| | | |
|---|---|---|
| KR | 10-1569278 B1 | 11/2015 |
| KR | 10-1605995 B1 | 4/2016 |

OTHER PUBLICATIONS

Juan Zhang et al; "Quantitative spectroscopic analysis of heterogeneous systems: chemometric methods for the correction of multiplicative light scattering effects", Rev Anal Chem, vol. 32, No. 2, 2013, pp. 113-125 (Total 14 pages), XP008180001, DOI: 10.1515/REVAC-2012-0037 [retrieved on Apr. 2, 2013].

M. Toiviainen et al; "Blind source separation in diffuse reflectance NIR spectroscopy using independent component analysis", Journal of Chemometrics, vol. 24, No. 7-8, May 27, 2010 (May 27, 2010), pp. 514-522 (Total 10 pages), XP055126170, ISSN: 0886-9383, 001: 10.1002/ceni. 1316.

Benjamin Bird et al; "Two step resonant Mie scattering correction of infrared micro-spectral data: human lymph node tissue", Journal of Biophotonics, vol. 3, No. 8-9, Apr. 22, 2010 (Apr. 22, 2010), pp. 597-608 (Total 12 pages), XP055149478, ISSN: 1864-063X, DOI: 10.1002/jbio.201000024.

Nils Kristian Afseth et al.; "Extended multiplicative signal correction in vibrational spectroscopy, a tutorial", Chemometrics and Intelligent Laboratory Systems, vol. 117, Aug. 1, 2012 (Aug. 1, 2012), pp. 92-99, (Total 8 pages) XP055267807, ISSN: 0169-7439, D0I:10.1016/j.chemolab.2012.03.004.

Peter Lasch: "Spectral pre-processing for biomedical vibrational spectroscopy and microspectroscopic imaging", Chemometrics and Intelligent Laboratory Systems, vol. 117, Aug. 1, 2012 (Aug. 1, 2012), pp. 100-114 (Total 16 pages), XP055397211, NL, ISSN: 0169-7439, D0I:10.1016/j.chemolab.2012.03.011.

* cited by examiner

METHOD OF ENABLING FEATURE EXTRACTION FOR GLUCOSE MONITORING USING NEAR-INFRARED (NIR) SPECTROSCOPY

CROSS-REFERENCE TO RELATED APPLICATIONS

This application claims priority from Indian Patent Application No. 201741010850, filed on Mar. 27, 2017 in the Indian Patent Office, and Korean Patent Application No. 10-2018-0026210, filed on Mar. 6, 2018 in the Korean Intellectual Property Office, the disclosures of which are incorporated herein by reference in their entireties.

BACKGROUND

1. Field

Apparatuses and methods consistent with exemplary embodiments relate to glucose monitoring, and more particularly relate to enabling feature extraction for glucose monitoring through Near-Infrared Spectroscopy.

2. Description of the Related Art

Glucose monitoring may be used to measure the level of glucose in a blood sample. The glucose monitoring may be performed either invasively or non-invasively. In the invasive method, the skin of a person is pierced to obtain the blood sample. In the non-invasive method, collection of the blood sample may not be required to measure the glucose level, and instead Mid-Infrared (Mid-IR) spectroscopy, Near-Infrared (NIR) spectroscopy, or Raman spectroscopy may be used. The NIR spectroscopy has been used for continuous glucose monitoring, in which NIR waves are generated to pass through the skin and a spectrum indicating absorption of the NIR waves by the blood underneath the skin is used in determining the glucose level. The absorption of the NIR waves is defined based on BEER-Lambert law:

$$A = \log\left(\frac{I}{I_0}\right) = \epsilon C d$$

Where $\epsilon$ is molecular extinction co-efficient,
C is concentration of component in sample, and
d is penetration depth.
If the blood is composed of different constituents, then overall absorption can be given as $$A = \epsilon_1 C_1 d + \epsilon_2 C_2 d + \ldots + \epsilon_n C_n d$$

The NIR absorption spectrum indicates absorption of several components such as water, fat, protein (Collagen and Keratin), Amino acids, elastin and Glucose. Therefore, $$A\_NIR = A\_Water + A\_Cholesterol + A\_Collagen + A\_Keratin + A\_elastin + A\_acid + A\_Glucose$$

Further, the concentration of glucose in an interstitial liquid can be approximated as $$C\_Glucose = A\_Glucose / A\_Water$$

Thus, glucose monitoring using NIR spectroscopy is very challenging as the values of glucose absorption is of several orders lesser than other constituents and many times, the glucose information is distorted due to noise components of the NIR data. The order of concentration of different constituents are shown in the below table.

| Constituent | Water | Fat | Protein | Elastin/Acid | Glucose |
|---|---|---|---|---|---|
| Order of concentration(−) | $10^{\wedge}0$ | $10^{\wedge}-1$ | $10^{\wedge}-3$ | $10^{\wedge}-3$ | $10^{\wedge}-4$ |

Therefore, there is a need for a method for removing the impacts caused by other constituents of the body and NIR spectrometers for effective glucose monitoring.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a method of extracting glucose feature, the method comprising: removing noise from a near-infrared (NIR) data; extracting a glucose signal from the NIR data; and removing temporal drift components from the extracted glucose signal.

The removing the noise comprises removing the noise from the NIR data using at least one of an Savitzky-Golay (SG) filter and a Fourier domain filtering.

The extracting the glucose signal comprises removing a signal component of a body composition other than a glucose from the NIR data.

The body composition other than the glucose comprises at least one of water, fat and protein.

The extracting the glucose signal comprises extracting the glucose signal based on an Extended Multiplicative Scatter Correction (EMSC) regression and data whitening.

The data whitening is performed to obtain an orthogonal component of a pure spectrum of a body composition including a glucose.

The EMSC regression is applied to resolve the NIR data into signal components of individual body compositions using the orthogonal component of the pure spectrum of the body composition generated by the data whitening.

The removing temporal drift components comprises differentiating and smoothing the extracted glucose signal, and removing the temporal drift components by applying a drift removal technique to the differentiated and smoothed glucose signal.

The removing temporal drift components by applying a drift removal technique comprises calculating the temporal drift components by differentiating and averaging the differentiated and smoothed glucose signal, and removing the calculated temporal drift components from the differentiated and smoothed glucose signal.

According to an aspect of another embodiment, there is provided a method of monitoring glucose including: filtering a near-infrared (NIR) data, which is obtained from a NIR light that is emitted to and returns from a user, by removing noise from the NIR data; extracting a glucose signal from the filtered NIR data by removing one or more body composition components from the filtered NIR data; removing temporal drift components from the extracted glucose signal; generating a data model for glucose prediction by regressing the extracted glucose signal from which the temporal drift components have been removed, based on an expected glucose signal; and predicting a glucose level of the user based on the generated data model.

The body composition components may include at least one of water, fat, proteins, and elastin.

The filtering may be performed using an Savitzky-Golay (SG) filter.

The filtering may be performed using a Fourier domain filtering.

The glucose signal may be extracted based on an Extended Multiplicative Scatter Correction (EMSC) regression and data whitening.

The data whitening may be performed to obtain orthogonal components of reference spectra of the body composition components.

The EMSC regression may be applied to resolve an absorption spectrum of the NIR light into individual components of glucose using orthogonal spectra generated by the data whitening.

The removing the temporal drift components may further include smoothing a differential of the extracted glucose signal by coarsely removing the temporal drift components from the extracted glucose signal.

The removing the temporal drift components may further include applying a fine drift removal method to the smoothed differential of the extracted glucose signal to remove a residual drift from the extracted glucose signal.

According to an aspect of another exemplary embodiment, there is provided a glucose monitoring device including: a filtering module configured to remove noise components from a near-infrared (NIR) data generated from a NIR spectrometer; an interferents removal module configured to extract a glucose signal from the NIR data by removing one or more body composition components, the body composition components comprising at least one of water component, fat, proteins, and elastin; and a feature extraction module configured to remove, from the extracted glucose signal, drift components caused due to a drift of the NIR spectrometer; wherein the glucose monitoring device may generate a data model for glucose prediction by regressing the extracted glucose signal from which the drift components have been removed, based on an expected glucose signal; and may predict a glucose level of a user based on the generated data model.

The filtering module may include a Savitzky-Golay (SG) filter and a Fourier domain filter to remove the noise components from the NIR data.

The interferents removal module may include: a data whitening module configured to obtain orthogonal components of reference spectra of the body composition components to perform an Extended Multiplicative Scatter Correction (EMSC) regression; an EMSC regression module configured to resolve the NIR data into one or more individual components of glucose; and a glucose signal extraction configured to extract the glucose signal from the NIR data from which the noise components have been removed.

The feature extraction module may include: a SG filter with differential module configured to smooth a differential of the extracted glucose signal; and a drift removal module configured to remove the drift components from the extracted glucose signal.

According to an aspect of another exemplary embodiment, there is provided a non-transitory computer readable storage medium storing a program that is executable by a computer to perform a method of monitoring glucose. The method may include: receiving a near-infrared (NIR) absorption spectrum indicating a plurality of body composition components of a user; filtering the NIR absorption spectrum to remove noise components from the NIR absorption spectrum; removing, from the NIR absorption spectrum, a signal indicating at least one of the plurality of body composition components other than glucose, and drift components to extract a glucose signal from the NIR absorption spectrum; regressing the extracted glucose signal to generate a glucose prediction model; and predicting a glucose level of the user based on the glucose prediction model.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
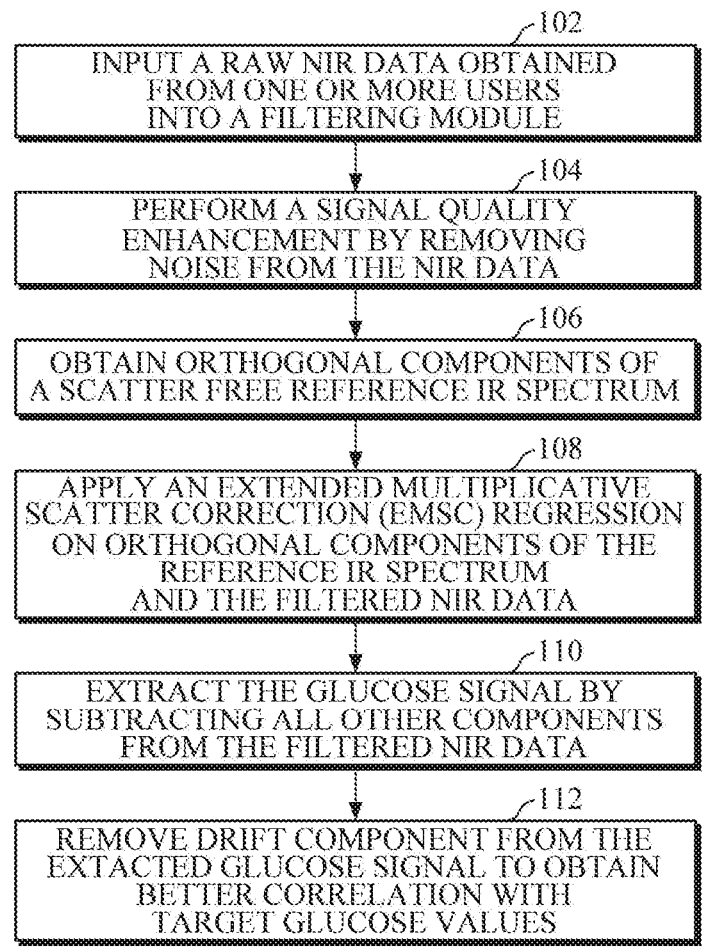
FIG. 1 is a flowchart illustrating a method of enabling feature extraction for glucose monitoring using near infrared spectroscopy, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The specification may refer to "an", "one" or "some" embodiment(s) in several locations. This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements and/or components, but do not preclude the presence or addition of one or more other features, integers, steps, operations, elements, components, and/or groups thereof. As used herein, the term "and/or" includes any and all combinations and arrangements of one or more of the associated listed items.

Expressions such as "at least one of," when preceding a list of elements, modify the entire list of elements and do not modify the individual elements of the list.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A NIR glucose meter described herein may be implemented as a software module or in the form of a hardware chip and be mounted in an electronic device. In this case, the electronic device may include a mobile phone, a smart phone, a notebook computer, a personal digital assistant (PDA), a portable multimedia player (PMP), a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

FIG. 1 is a flowchart illustrating a method of enabling feature extraction for glucose monitoring using near infrared spectroscopy, according to an exemplary embodiment. In operation 102, a raw near-infrared (NIR) data associated with a glucose absorption spectrum of one or more users is received, and in operation 104, the raw NIR data is filtered by removing noise from the raw NIR data. The noise may be caused when a NIR light is scattered while the NIR light is emitted to, passes through, and returns from the skin. In operation 106, orthogonal components of a scatter free reference IR spectrum are obtained, and in operation 108, an Extended Multiplicative Scatter Correction (EMSC) regression is applied to the orthogonal components of the scatter free reference IR spectrum and the filtered NIR data. In operation 110, a glucose signal is extracted from the filtered NIR data by removing one or more body composition components, in operation 104. In one exemplary embodiment, the body composition components include at least one of water, fat, and protein (ex. collagen, keratin, and elastin, etc.). In operation 112, removal of temporal drift components from the extracted glucose signals is performed. A data model for glucose prediction is generated by regressing the extracted glucose features after drift removal with an expected glucose values taken for calibration. The glucose values of the new NIR data are predicted using the generated data model.

Figure 2:
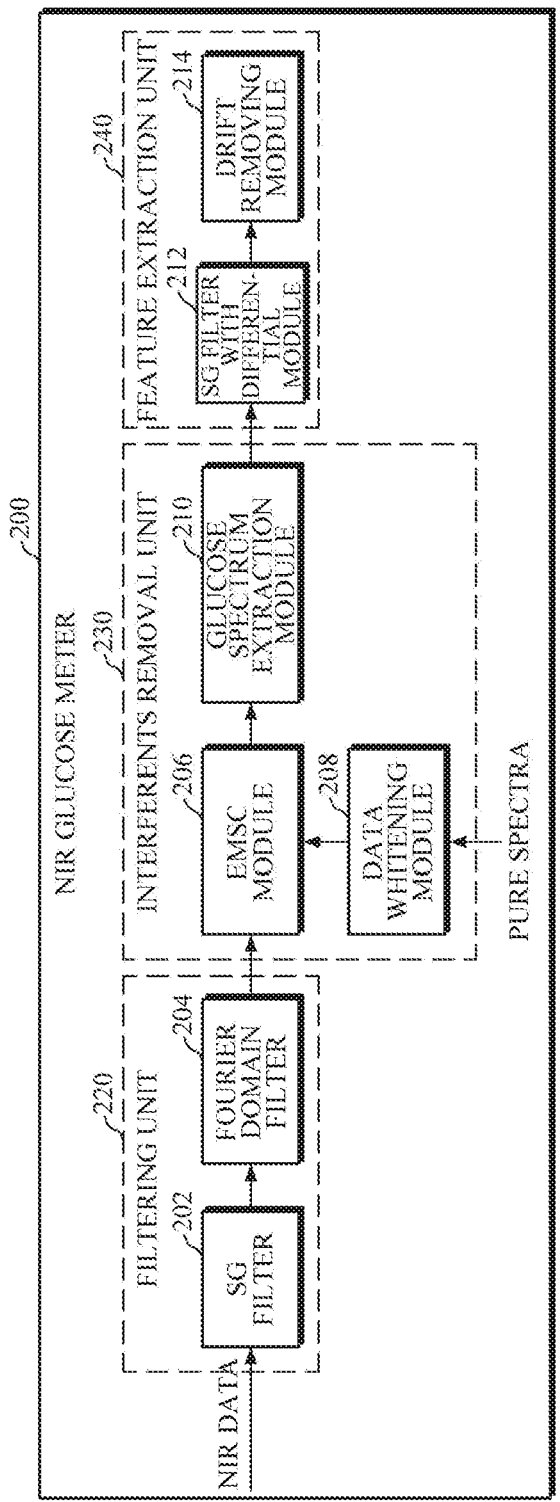
FIG. 2 is a block diagram illustrating a NIR glucose meter according to an exemplary embodiment.
Figure 3A:
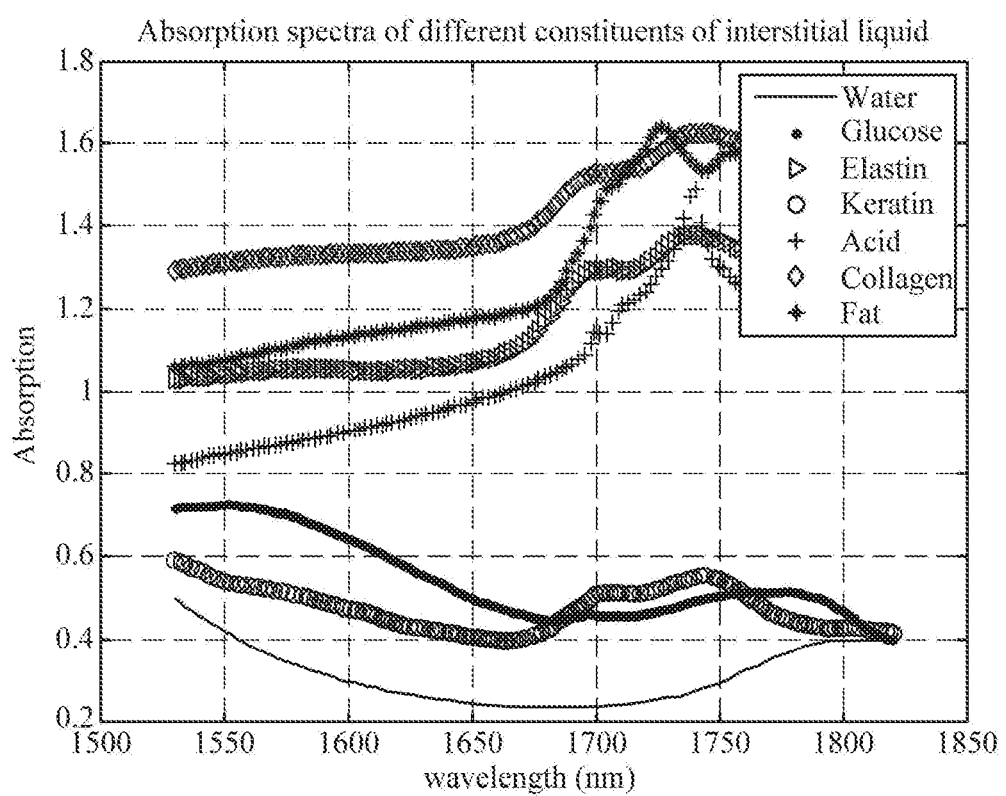
FIG. 3A illustrates NIR absorption spectra of different constituents of blood, according to an exemplary embodiment.

FIG. 2 is a block diagram illustrating a NIR glucose meter 200 according to an exemplary embodiment. A particular skin region is illuminated with near-infrared (NIR) light using a NIR spectrometer of the NIR glucose meter 200. The NIR light may be partially absorbed and scattered according to its interaction with the constituents of tissue beneath the particular skin region before reflected back to a NIR photodetector in the NIR glucose meter 200. The normalized absorption of NIR spectrum by different constituents is shown in FIG. 3A. The reflected light contains quantitative information of the constituents of the tissue including water, fat, protein and glucose. The reflected light containing NIR spectrum data is made to pass through the NIR glucose meter 200. As shown in FIG. 2, the NIR glucose meter 200 includes a filtering unit 220, an interferents removal unit 230 and a feature extraction unit 240. The filtering unit 220, the interferents removal unit 230, and the feature extraction unit 240 may be implemented with one or more processors.

The filtering unit 220 may remove unwanted noises from the NIR spectrum data. In this case, the NIR spectrum data may be a near-infrared (NIR) absorption spectrum data of skin that is obtained by measuring NIR emitted toward the skin of the user. However, the NIR spectrum data is not limited thereto, and may be a NIR transmittance spectrum data of skin or NIR reflectance spectrum data of a skin. According to an exemplary embodiment, the filtering unit 220 may use baseline correction algorithm and/or smoothing algorithm to remove unwanted noises from the NIR spectrum data. For example, the filtering unit 220 may use Savitzky-Golay smoothing, Fourier domain filtering, and moving average, etc.

The filtering unit 220 includes a Savitzky-Golay (SG) filter 202 and a Fourier domain filter 204 to remove unwanted noises from the NIR spectrum data. The SG filter 202 may remove spikes present in the NIR spectrum data received from the NIR spectrometer and the Fourier domain filter 204 reduces the impact of interferents of the NIR spectrum data as well as the noise added in the areas where there is no overlap of signal corresponding to glucose.

The noise removing process using the filtering unit is further explained as follows. In one exemplary embodiment, an NIR spectrum signal x(n) containing raw NIR data is inputted to the SG filter 202. The SG filter 202 is a polynomial fit (n) filter of order N. The SG filter 202 smoothens the NIR spectrum signal x(n) by minimizing the sum of square of errors (E) for 2M+1 samples, wherein the error calculation is given as $$E = \sum_{n=-M}^{M} (p(n) - x(n))^2$$

$$p(n) = \sum_{k=0}^{N} a_k n^k$$

Where n is the sample number.

By minimizing E with respect to different $a_k$, $k \in (0, N)$, the NIR spectrum signal x(n) is smoothened by convoluting first row of matrix H with signal vector of 2M+1 samples around the sample of interest.

$$H = (A^T A)^{-1} A^T \text{ where } A_{n,i} = n^i, 0 \leq i < N, -M \leq n \leq M$$

Where N is order of polynomial and 2M+1 samples considered for measuring error to be minimized.

Thus, a smoothed output $x_{sg}(n)$ of the SG filter with zero differential order is obtained as follows $$x_{sg}(n) = \sum_{m=-M}^{M} H_{0,-m} x(n+m)$$

$H_{0,m}$ represents a first row of matrix H

The resultant smoothened signal of NIR spectrum is sent to the Fourier domain filter 204. The Fourier domain filter 204 reduces the impact of interferents of the NIR spectrum as well as the noise added in the time window where there is no significant overlap of signal corresponding to glucose.

Figure 3B:
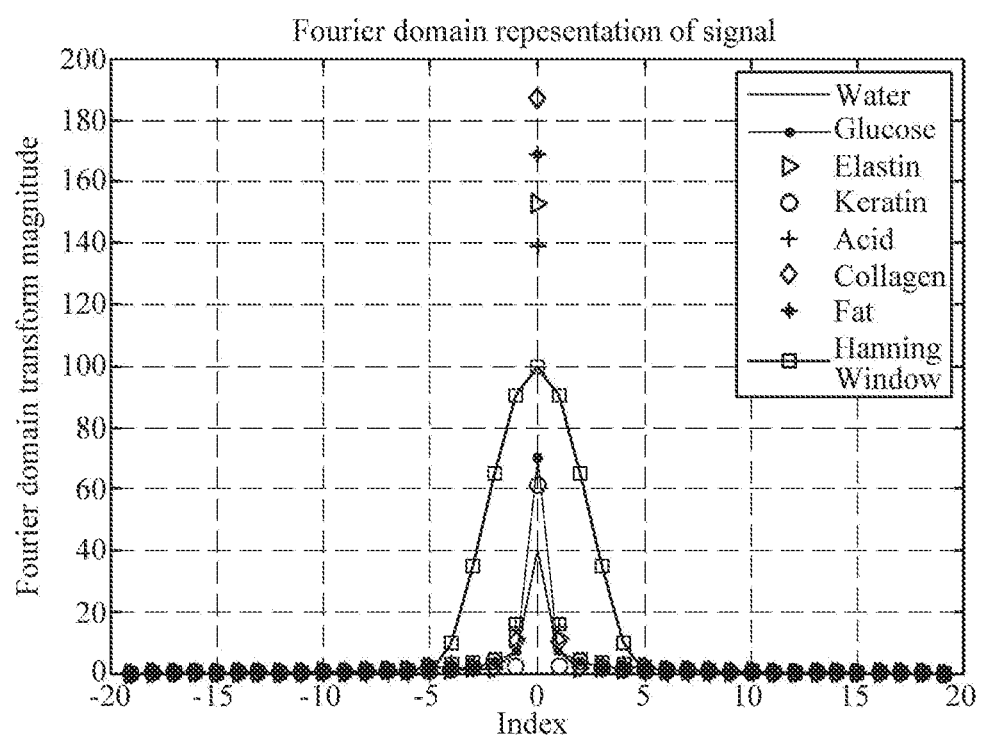
FIG. 3B illustrates a Fourier domain signal for each constituent of tissue containing interstitial liquid, according to an exemplary embodiment.

The NIR spectrum received from the NIR spectrometer is in the range 1530 nm to 1830 nm in wavelength. The NIR spectrum of the above range is represented by few samples of a dominant signal in the time domain. This case is valid for all of the interferents in the signal. An exemplary Fourier domain representation of signal in the time domain for each constituent of tissue containing interstitial liquid is shown in FIG. 3B. The Fourier domain filter 204 then applies a Hanning window to suppress the noise. For example, the Fourier domain filter 204 may transform time domain signal $x_{sg}(n)$ into Fourier domain as shown below.

$$X(K) = FFT(x_{sg}(n))$$

The NIR spectrum is then transformed into Fourier domain and multiplied with a Hanning window as shown below.

$$x_{fd}(t) = IFFT(X(K) * \text{Hanning}(N_{win})),$$

where $N_{win}$ is the window size.

It is to be noted that the Hanning window can be replaced by any Gaussian pulse shape, Raised Cosine pulse shape or any other smoothing response.

The interferents removal unit 230 may extract a glucose signal from the NIR data by removing one or more body composition components. According to an exemplary embodiment, the interferents removal unit 230 may resolve the skin spectrum into individual component spectrums using a pure spectrum of each body component and extract the glucose signal based on the resolved individual component spectrums. For example, the interferents removal unit 230 may use extended multiplicative scatter algorithm, gradient descent, least square, pseudo inverse, singular value decomposition, etc.

The interferents removal unit 230 includes an Extended Multiplicative Scatter Correction (EMSC) module 206 and a data whitening module 208 and a glucose spectrum extraction module 210. The EMSC module 206 includes an algorithm executed to obtain a spectrum of a glucose signal from the NIR spectrum that is filtered by the SG filter 202 and the Fourier domain filter 304. The filtered NIR spectrum may be absorption spectra of a plurality of body constituents. The EMSC module 206 receives orthogonal spectra (Q) from the data whitening module 208. The EMSC module 206 receive orthogonal spectra of different interferents and regress for compositions in the NIR data. Then, concentrations of components obtained from the NIR data is subtracted from the NIR data to obtain the glucose signal. The process of EMSC and data whitening is discussed in detail hereinafter.

In order to perform the EMSC algorithm, a data whitening module 208 produces orthogonal spectral components Q that are orthogonal to each other such that a pure spectra P of body compositions can be obtained by linear combinations of the orthogonal spectral components Q. The pure spectra P are represented as $P = [p_0 p_1 \ldots p_{n-1}]$, where $p_k$ is a column vector representing pure spectrum $k^{th}$ body constituent. Matrix P contains pure spectra of all body constituents (e.g., water, fat, collagen, proteins) including glucose. The pure spectrum may be an absorption spectrum of pure material (e.g., collagen, elastin, and keratin).

Figure 4A:
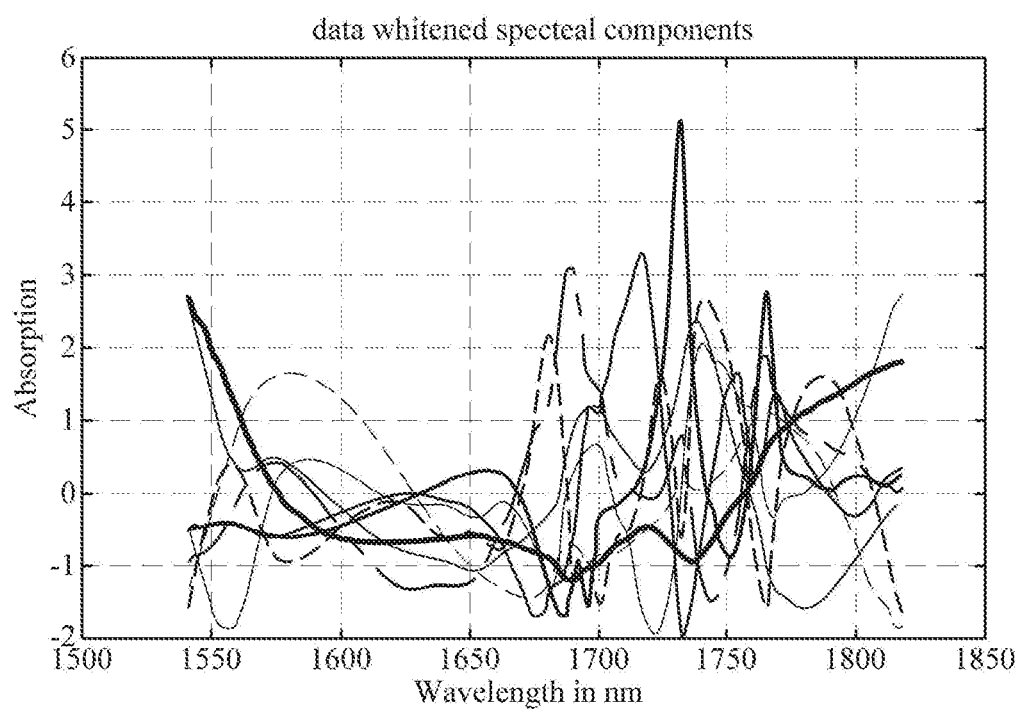
FIG. 4A illustrates NIR absorption spectra of different constituents of interstitial liquid, according to an exemplary embodiment.

The pure spectra of body constituents P is sent to the data whitening module 208 that obtains $\overline{P}$ by performing mean and standard deviation normalization of pure component spectra X. An exemplary absorption of data whitened spectral components is shown in FIG. 4A. For example, the data whitening module 208 may obtain $\overline{P}$ as shown below.

$$\overline{P}_i = \frac{P_i - E(P_i)}{std(P)}, \forall i$$

The $\overline{P}$ is then transformed into an orthogonal component Q by data whitening process as follows $$Q = ED^{-\frac{1}{2}}E'\overline{P} = Z\overline{P}, Z = ED^{-\frac{1}{2}}E'$$

Where E and D are Eigen vector matrix and diagonal matrix of Eigen values of $E(\overline{P}'\overline{P})$, which results in $$E(Q'Q) = I$$

Figure 4B:
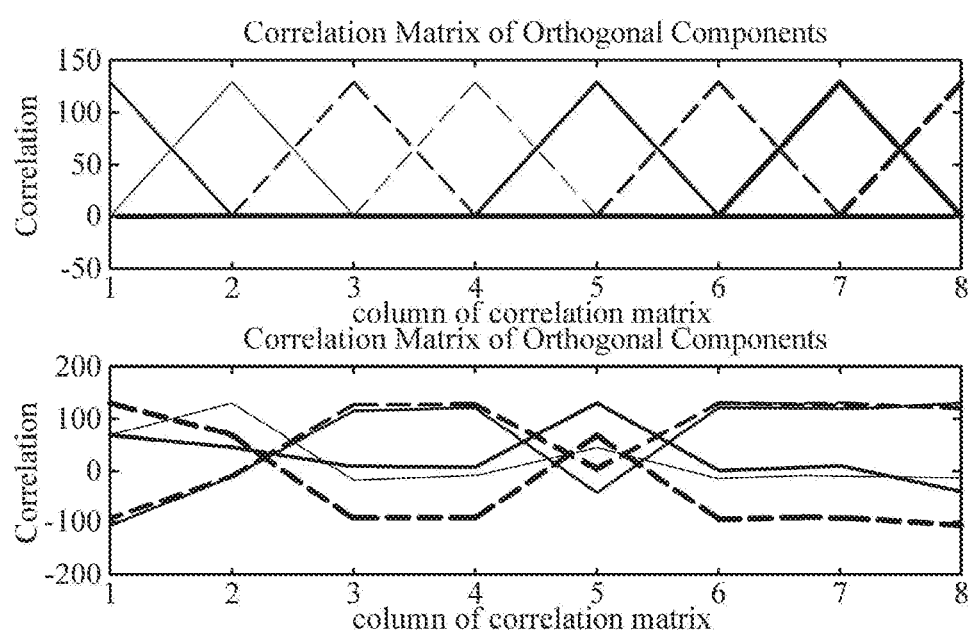
FIG. 4B illustrates correlation matrices of orthogonal components and pure spectral components, according to an exemplary embodiment.

An exemplary correlation matrix of orthogonal components Q is shown in FIG. 4B.

In one exemplary embodiment, the algorithm present in the EMSC module 206 resolves a given spectrum $x_{fd}(n)$ after noise filtering into N orthogonal spectra Q components obtained from data whitening module 208.

It may be assumed that $x_{fd}(n)$ is any noise filtered NIR spectrum including pure components P that has orthogonal components generated by the data whitening module 208 is Q. Then $x_{fd}(n)$ can be resolved into orthogonal spectra Q components as follows $$x_{fd}(n) = a_0 q_0(n) + a_1 q_1(n) + \ldots + a_{n-1} q_{m-1}(n)$$

Where $a_0, a_1, \ldots, a_{m-1}$ are strengths of independent components. The EMSC module 206 may estimate the weights $a_0, a_1, \ldots, a_{m-1}$ using gradient descent, east square, pseudo inverse, singular value decomposition, etc.

The glucose spectrum extraction module 210 may extract the glucose spectrum by removing body composition components except a glucose from $x_{fd}(n)$. For example, when the orthogonal spectrum of the glucose is $q_0$ and the strength of the glucose is $a_0$, the glucose spectrum extraction module 210 may extract the glucose spectrum as follows.

$$x^e_{glucose}(n) = x_{fd}(n) - \sum_{k=1}^{m-1} a_k q_k(n)$$

In turn, a differential $d^{th}$ of the estimated spectrum $X_{glucose}^e$ is obtained by using the SG-filter 202 one more time.

$$X^d_{feature}(n) = \sum_{m=-M}^{M} H_{d,-m} X^e_{glucose}(n+m)$$

Once the interferents removal unit 230 extracts the glucose spectrum, the extracted glucose spectrum is inputted to the feature extraction unit 240 that uses machine learning algorithms like Principal component regression (PCR) or Partial Least square regression (PLSR). The feature extraction unit 240 include a SG filter with differential module 212 and a drift removing module 214. The SG filter with differential module 212 is another filter that smoothens the extracted glucose spectrum. FIGS. 5A to 5D illustrate correlations of extraction feature and glucose values after drift removal, according to one exemplary embodiment. The SG filter with differential module 212 may obtain a smoothed version of the differential $d^{th}$ of the extracted glucose feature in a frequency domain. The glucose feature may be enhanced in the glucose spectrum and a baseline drift of the NIR spectrum of the differential $d^{th}$ may be coarsely eliminated, by using the SG filter with differential module 212.

In another exemplary embodiment, the drift removing module 314 may remove a residual baseline drift after applying the SG filter with differential. φ may be a N×P feature matrix having P features corresponding to N observations of glucose value in each row. Each row of φ includes extracted glucose features ($x_{glucose}^d$) of one raw NIR spectrum.

Any given element of φ is associated with a wavelength λ and time t, represented as $$\phi(t,\lambda) = I(\lambda) + a_\lambda * G(t) + \text{drift}(t,\lambda)$$

Where φ(t,λ) is a time varying feature $x_{glucose}^d(n)$ and I is non-time varying interference which could be combination of several residual body spectra, G is glucose value at time t, drift(t,λ) is temporal drift components of a given λ. $a_\lambda$, β are constants.

For a given λ, differentiating φ(t,λ) with respect to time, the following equations are obtained:

$$\frac{d\phi(t,\lambda)}{dt} = \alpha_\lambda * G'(t) + \text{drift}'(t,\lambda)$$

$$\text{mean}\left(\frac{d\phi(t,\lambda)}{dt}\right) = \text{driftmean}(\lambda) + K,$$

$$\text{driftmean}(\lambda) = \text{mean}(\text{drift}'(t,\lambda))$$

Here, K=$a_\lambda$*mean(G'(t))=0, approx, when the glucose variations sum to zero.

Each wavelength is compensated for drift as $$\hat{\phi}(\lambda) = \phi(\lambda) - \text{driftmean}(\lambda) * j$$

Here, j corresponds to j^th observation of glucose feature. The $\hat{\pi}(\lambda)$ obtained for both training and prediction data is sent to PCR or PLSR or any other machine learning algorithm for regression.

That is, the feature extraction unit 240 may remove temporal drift components from the extracted glucose signal by differentiating the glucose features ($x_{glucose}^d$), averaging the differentiated glucose features $$\left(\frac{d\phi(t,\lambda)}{dt}\right),$$

calculating an average of the temporal drift components (driftmean(λ)), and removing the average of the temporal drift components (driftmean(λ)) from the glucose features ($x_{glucose}^d$).

For clarity purposes, the method of presenting calibration and training data to a machine learning algorithm is presented herewith. The raw NIR data of one person taken on day 1 is used as calibration data $x_{cal}(n)$. The calibration data $x_{cal}(n)$ is submitted to the feature extraction unit in FIG. 2 which gives the output as $\widehat{\phi_{cal}(\lambda)}$. Each row of $\widehat{\phi_{cal}(\lambda)}$ represents an excreted glucose feature of one instance of the NIR spectrum. $Y_{cal}$ represents labeled glucose values measured with any other established techniques (e.g., blood glucose test) corresponding to given NIR spectra$x_{cal}(n)$. Matrices [$\widehat{\phi_{cal}(\lambda)}$), $Y_{cal}$] are submitted to a machine learning algorithm and a model for glucose values is built based on the machine learning algorithm. The raw NIR data of the same or a different person taken on day 2 is prediction data $x_{pred}(n)$. The prediction data $x_{pred}(n)$ is submitted to the feature extraction unit in FIG. 2 which gives the output as $\widehat{\phi_{cal}(\lambda)}$). This $\widehat{\phi_{cal}(\lambda)}$) is then submitted to the model generated by the machine learning algorithm which in turn predicts glucose values corresponding to $\widehat{\phi_{cal}(\lambda)}$).

Figure 5A:
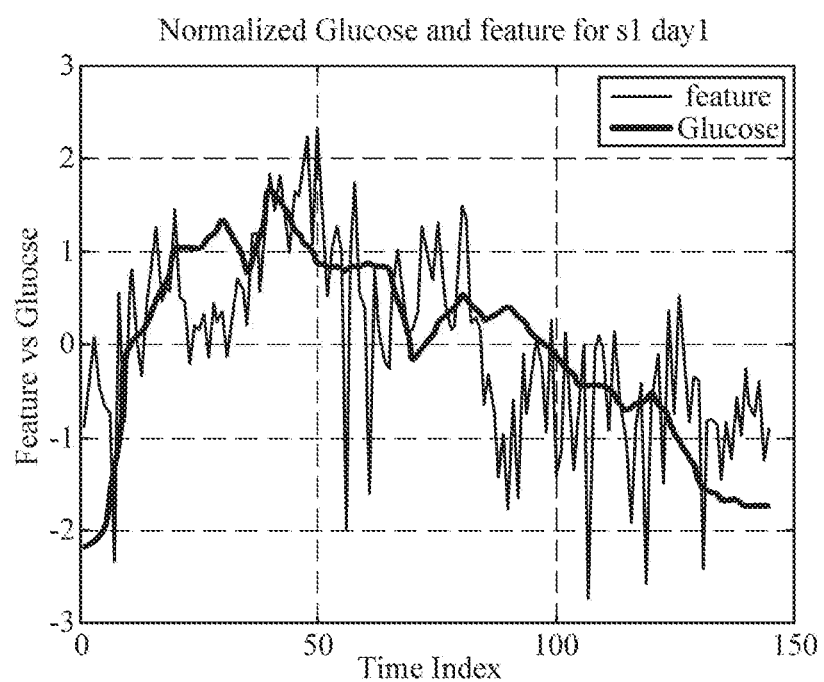
FIGS. 5A, 5B, 5C, and 5D illustrate correlations of extraction feature and glucose values after drift removal, according to an exemplary embodiment.
Figure 5B:
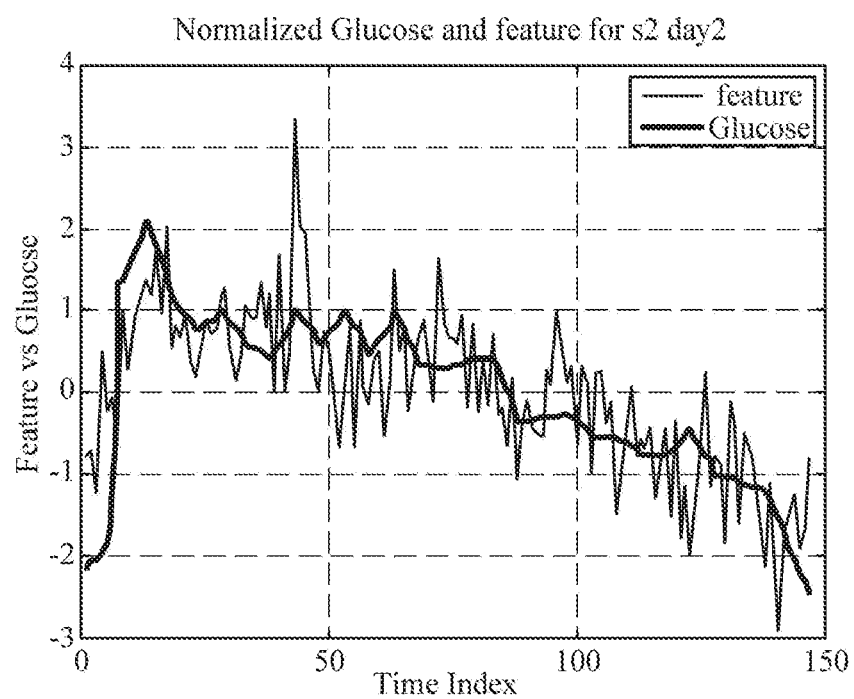
Figure 5C:
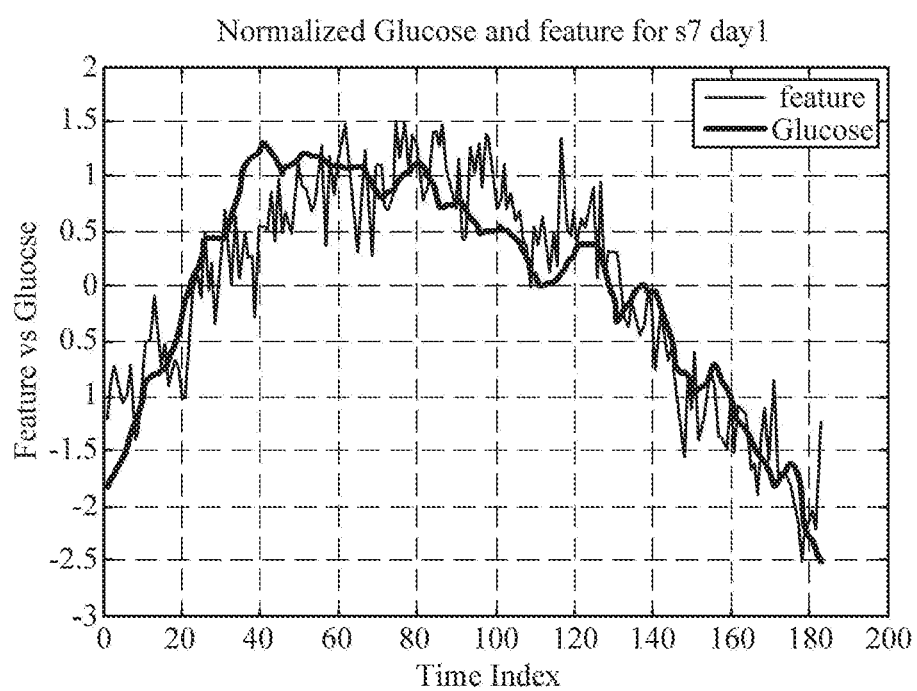
Figure 5D:
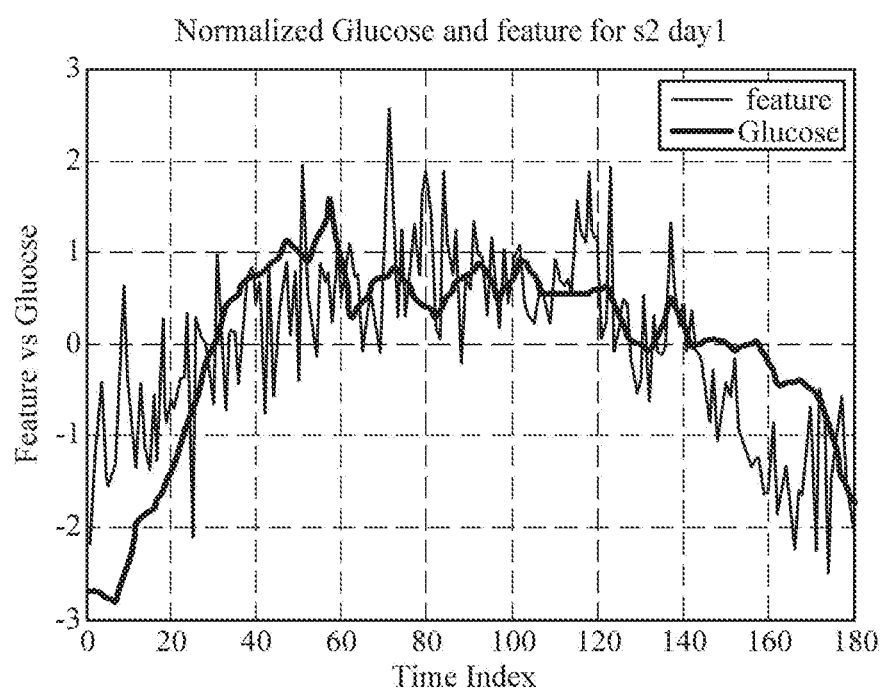
Figure 6A:
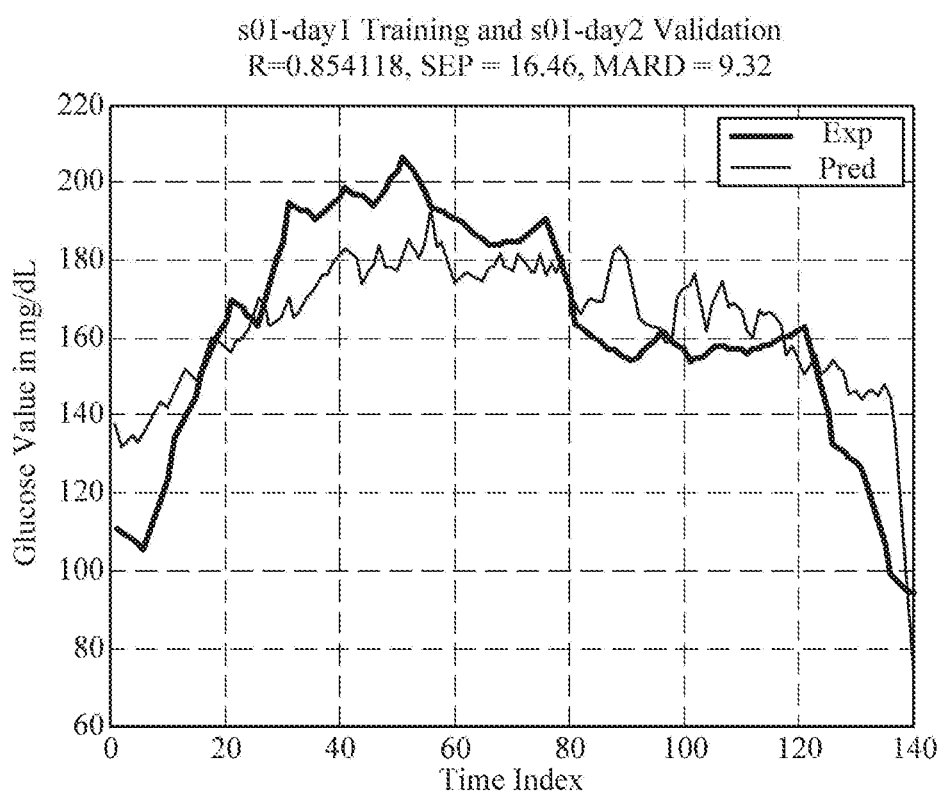
FIGS. 6A, 6B and 6C illustrate results of predicted glucose values using principal component regression (PCR), according to an exemplary embodiment.
Figure 6B:
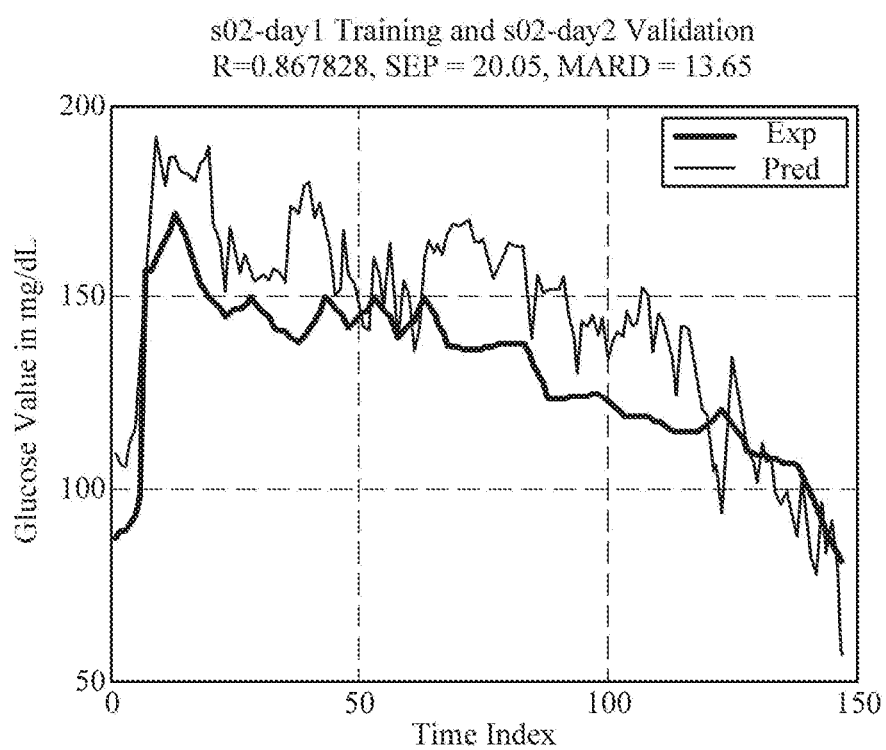
Figure 6C:
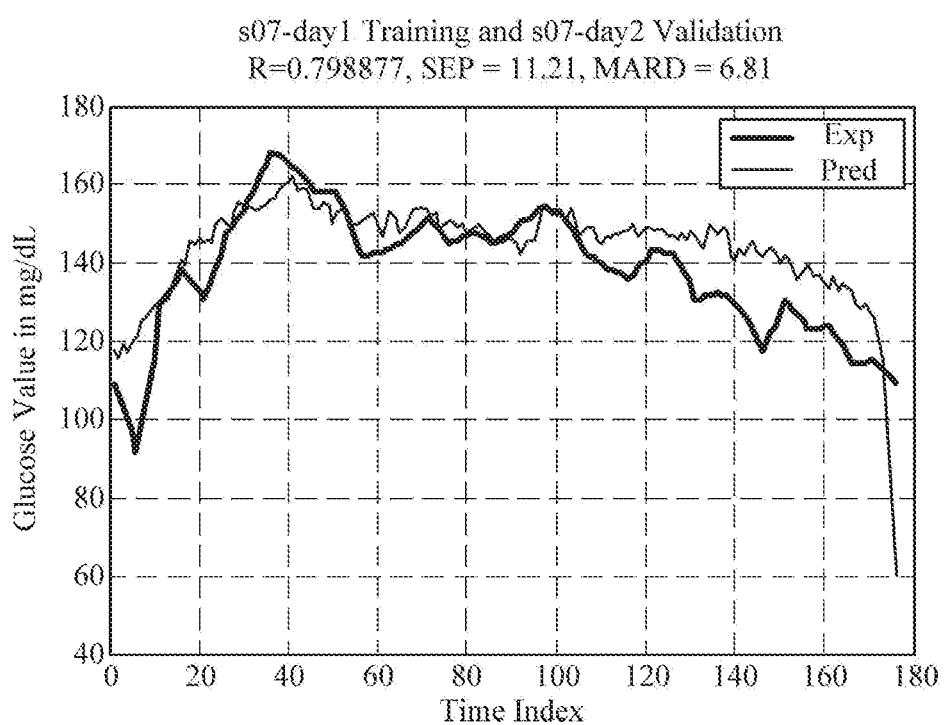

FIGS. 6A, 6B and 6C illustrate results of predicted glucose values using principal component regression (PCR), according to one exemplary embodiment. As shown in FIGS. 6A and 6B, s1, s2, ... s7 are the subjects or people considered for collecting the calibration and prediction data. For example, the raw NIR data collected from s1 (on day 1) for about 2 hours on every minute basis is provided to glucose meter for calibration and prediction model for glucose is generated. The raw NIR data for s1 on another day (day 1) is generated and submitted for prediction. FIG. 6A shows the plot of expected and predicted glucose values of s1 on day 2. The Pearson correlation of expected and predicted values R, Standard Error of prediction between expected and predicted values SEP, and mean absolute relative difference MARD of expected and predicted values of s1 on day 2 are listed in the title of the plot. For the same experiment, FIG. 5A shows a extracted normalized feature value following normalized glucose values. FIG. 6B to 6C show similar experiment results with different samples for calibration and prediction.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of extracting glucose feature, the method comprising:
   obtaining, by a spectrometer, a near-infrared (NIR) data;
   filtering the NIR data by removing noise from the NIR data;
   obtaining orthogonal components of a reference glucose spectrum;
   applying an Extended Multiplicative Scatter Correction (EMSC) regression to the reference glucose spectrum to resolve the reference glucose spectrum into orthogonal components;

extracting a glucose signal from the filtered NIR data by removing the orthogonal components from the filtered NIR data; and removing, from the extracted glucose signal, temporal drift components that are caused due to a drift of the spectrometer.

2. The method of claim 1, wherein the filtering the NIR data comprises removing the noise from the NIR data using a Savitzky-Golay (SG) filter.

3. The method of claim 1, wherein the extracting the glucose signal comprises removing, from the filtered NIR data, a signal component corresponding to a blood component other than a glucose.

4. The method of claim 3, wherein the blood component other than the glucose comprises at least one of water, fat and protein.

5. The method of claim 1, wherein the removing temporal drift components comprises differentiating and smoothing the extracted glucose signal, and removing the temporal drift components by applying a drift removal technique to the differentiated and smoothed glucose signal.

6. The method of claim 5, wherein the removing temporal drift components by applying the drift removal technique comprises calculating the temporal drift components by differentiating and averaging the differentiated and smoothed glucose signal, and removing the calculated temporal drift components from the differentiated and smoothed glucose signal.

7. A method of monitoring glucose, the method comprising:
  filtering a near-infrared (NIR) data, which is obtained by a spectrometer from a NIR light that is emitted to and returns from a user, by removing noise from the NIR data;
  obtaining orthogonal components of a reference glucose spectrum;
  applying an Extended Multiplicative Scatter Correction (EMSC) regression to the reference glucose spectrum to resolve the reference glucose spectrum into orthogonal components;
  extracting a glucose signal from the filtered NIR data by removing the orthogonal components from the filtered NIR data;
  removing, from the extracted glucose signal, temporal drift components that are caused due to a drift of the spectrometer;
  generating a data model for glucose prediction by regressing the extracted glucose signal from which the temporal drift components have been removed, based on an expected glucose signal; and
  predicting a glucose level of the user based on the generated data model.

8. The method of claim 7, wherein the filtering is performed using an Savitzky-Golay (SG) filter.

9. The method of claim 7, wherein the filtering is performed using a Fourier domain filtering.

10. The method of claim 7, wherein the removing the temporal drift components further comprises smoothing a differential of the extracted glucose signal by coarsely removing the temporal drift components from the extracted glucose signal.

11. The method of claim 10, wherein the removing the temporal drift components further comprises applying a fine drift removal method to the smoothed differential of the extracted glucose signal to remove a residual drift from the extracted glucose signal.

12. A glucose monitoring device, comprising:
  a filtering module configured to filter a near-infrared (NIR) data generated from a NIR spectrometer by removing noise from the NIR data;
  an interferents removal module configured to:
    obtain orthogonal components of a reference glucose spectrum;
    apply an Extended Multiplicative Scatter Correction (EMSC) regression to the reference glucose spectrum to resolve the reference glucose spectrum into orthogonal components;
    extract a glucose signal from the filed NIR data by removing the orthogonal components from the filtered NIR data; and
  a feature extraction module configured to remove, from the extracted glucose signal, drift components caused due to a drift of the NIR spectrometer;
  wherein the glucose monitoring device is configured to generate a data model for glucose prediction by regressing the extracted glucose signal from which the drift components have been removed, based on an expected glucose signal; and predict a glucose level of a user based on the generated data model.

13. The glucose monitoring device of claim 12, wherein the filtering module comprises a Savitzky-Golay (SG) filter and a Fourier domain filter to remove the noise from the NIR data.

14. The glucose monitoring device of claim 12, wherein the feature extraction module comprises:
  a SG filter with differential module configured to smooth a differential of the extracted glucose signal; and
  a drift removal module configured to remove the drift components from the extracted glucose signal.

* * * * *